(12) United States Patent
Kolberg

(10) Patent No.: US 12,089,812 B2
(45) Date of Patent: Sep. 17, 2024

(54) ENDOSCOPE HEAD, ENDOSCOPE AND ALBARRAN LEVER HOLDING MEMBER

(71) Applicant: DIGITAL ENDOSCOPY GMBH, Friedberg (DE)

(72) Inventor: Stefan Kolberg, Friedberg (DE)

(73) Assignee: DIGITAL ENDOSCOPY GMBH, Friedberg (DE)

( * ) Notice: Subject to any disclaimer, the term of this patent is extended or adjusted under 35 U.S.C. 154(b) by 570 days.

(21) Appl. No.: 17/319,551

(22) Filed: May 13, 2021

(65) Prior Publication Data

US 2021/0259525 A1   Aug. 26, 2021

Related U.S. Application Data

(62) Division of application No. 16/087,903, filed as application No. PCT/EP2017/069800 on Aug. 4, 2017, now Pat. No. 11,058,284.

(30) Foreign Application Priority Data

Aug. 11, 2016 (DE) ..................... 10 2016 114 881.4

(51) Int. Cl.
*A61B 1/00* (2006.01)
*A61B 1/018* (2006.01)
(Continued)

(52) U.S. Cl.
CPC ...... *A61B 1/00101* (2013.01); *A61B 1/00181* (2013.01); *A61B 1/018* (2013.01);
(Continued)

(58) Field of Classification Search
CPC ............ A61B 1/00101; A61B 1/00181; A61B 1/018; A61B 1/00098; A61B 1/00135;
(Continued)

(56) References Cited

U.S. PATENT DOCUMENTS

| 4,436,087 A | 3/1984 | Ouchi |
|---|---|---|
| 6,338,717 B1 | 1/2002 | Ouchi |

(Continued)

FOREIGN PATENT DOCUMENTS

| DE | 199 62 209 A1 | 6/2000 |
|---|---|---|
| EP | 2 138 092 A1 | 12/2009 |

(Continued)

OTHER PUBLICATIONS

International Search Report issued in International Bureau of WIPO Patent Application No. PCT/EP2017/069800, dated Nov. 23, 2017.

(Continued)

*Primary Examiner* — Michael J Carey
*Assistant Examiner* — Christen A. Sharpless
(74) *Attorney, Agent, or Firm* — GREENBLUM & BERNSTEIN, P.L.C.

(57) ABSTRACT

The invention refers to an ultrasonic endoscope comprising an endoscope head body that is disposed on a distal side of an insertion portion of the ultrasonic endoscope and is provided with an Albarran lever chamber which is open continuously at an end portion and a side surface of the endoscope head body; a convex-shaped ultrasonic head that is disposed at the end portion of the endoscope head body and capable of transmitting and receiving ultrasonic signals in a lateral viewing direction corresponding to the side surface of the endoscope head body; and an Albarran lever that is disposed in the Albarran lever chamber and pivotally fixed to be rotatable.

6 Claims, 14 Drawing Sheets

(51) Int. Cl.
   *A61B 1/273* (2006.01)
   *A61B 8/12* (2006.01)
(52) U.S. Cl.
   CPC ....... *A61B 1/00098* (2013.01); *A61B 1/00135* (2013.01); *A61B 1/00137* (2013.01); *A61B 1/2736* (2013.01); *A61B 8/12* (2013.01)
(58) Field of Classification Search
   CPC ..... A61B 1/00137; A61B 1/2736; A61B 8/12; A61B 1/273; A61B 1/00071; A61B 1/00142; A61B 1/31
   See application file for complete search history.

(56) References Cited

U.S. PATENT DOCUMENTS

| | | | |
|---|---|---|---|
| 6,582,357 B2 | 6/2003 | Ouchi et al. | |
| 7,946,993 B2 | 5/2011 | Kohno | |
| 9,380,996 B2 | 7/2016 | Hiraoka | |
| 2002/0101788 A1 | 8/2002 | Petsch | |
| 2005/0228289 A1* | 10/2005 | Kohno | A61B 1/018 600/463 |
| 2005/0234297 A1* | 10/2005 | Devierre | A61B 1/00087 600/129 |
| 2007/0038089 A1 | 2/2007 | Hatano et al. | |
| 2009/0318831 A1 | 12/2009 | Aoki et al. | |
| 2016/0270637 A1* | 9/2016 | Tanaka | A61B 1/00098 |

FOREIGN PATENT DOCUMENTS

| | | | |
|---|---|---|---|
| EP | 2 878 272 A1 | 6/2015 | |
| JP | H04-314439 A | 11/1992 | |
| JP | H06-315458 A | 11/1994 | |
| JP | H10-146314 A | 6/1998 | |
| JP | 3159464 B2 | 4/2001 | |
| JP | 2002017655 A * | 1/2002 | |
| JP | 2007-215634 A | 8/2007 | |
| JP | 2007215634 A * | 8/2007 | A61B 1/00098 |
| WO | 2014/038638 A1 | 3/2014 | |

OTHER PUBLICATIONS

Written Opinion of the International Searching Authority issued in International Bureau of WIPO Patent Application No. PCT/EP2017/069800, dated Nov. 23, 2017, along with an English translation thereof.
U.S. Appl. No. 17/319,550 to Kolberg, filed May 13, 2021.
U.S. Appl. No. 17/319,556 to Kolberg, filed May 13, 2021.
Notice of Reasons for Refusal issued on Jun. 22, 2022 for Japanese family member JP2021-120763, together with an English-language translation.

* cited by examiner

ENDOSCOPE HEAD, ENDOSCOPE AND ALBARRAN LEVER HOLDING MEMBER

CROSS-REFERENCE TO RELATED APPLICATIONS

The present application is a divisional of U.S. patent application Ser. No. 16/087,903 filed Sep. 24, 2018, which is a U.S. National Stage Application of International Patent Application No. PCT/EP2017/069800 filed Aug. 4, 2017, which claims the benefit of German Patent Application No. 10 2016 114 881.4 filed Aug. 11, 2016. The disclosure of each of the above-noted applications is expressly incorporated herein by reference in its entirety.

The present invention relates to an endoscope head comprising an endoscope head body, in which at least one working channel is formed and in which an Albarran lever capable of being pivoted is provided at the distal working channel end portion, and to an endoscope comprising such an endoscope head. Further, the present invention relates to an Albarran lever holding member for an endoscope.

Such an endoscope head body can, for example, be applied to a duodenoscope, i.e. an endoscope for examining e.g. the esophagus or the duodenum, the bile duct, the gall bladder, the pancreatic duct, the pancreas, etc.

By means of the duodenoscope it is possible to reach the duodenum through the esophagus, the stomach and the pylorus.

The duodenoscope comprises optics (illumination means and camera) directed to the side (lateral). This may complicate inserting and advancing the duodenoscope through the esophagus since a "forward-facing" observation is not easily possible. Only the stomach or the duodenum provides enough room to bend the distal end of the duodenoscope by about 90° so as to enable forward viewing.

Further, at the working channel outlet, the duodenoscope comprises an Albarran lever which, by means of pivoting, enables a precise deflection of the tools advanced through the working channel.

After the duodenoscope has been used, it is subjected to reprocessing. The reprocessing must reliably prevent microorganisms such as bacteria, viruses, fungi, worms and spores from being transmitted. In the course of reprocessing, the duodenoscope is initially cleaned manually in order to remove all traces of organic material or chemical residues. After cleaning, a mechanical disinfection or sterilization is carried out.

It is the object of the present invention to provide an endoscope head comprising an endoscope head body, which is easy to clean but also versatile. Moreover, an endoscope and an Albarran lever holding member for an endoscope shall be provided.

This object is achieved by an endoscope head comprising an endoscope head body including the features of claim 1. Advantageous further developments are described in the dependent claims.

Thus, an endoscope head has been provided which comprises an endoscope head body, in which at least one working channel is formed, wherein an Albarran lever capable of being pivoted is provided at the distal working channel end portion.

The Albarran lever can be inserted at the endoscope head body laterally to the axis of the endoscope head body and removed from the endoscope head body laterally to the axis of the endoscope head body. Thus, the Albarran lever can be removed from the endoscope head body laterally to the axis of the endoscope head body and is easily detachable from the endoscope head body.

The endoscope head may comprise a housing sheath part at which the Albarran lever is pivotally disposed, wherein the housing sheath part can be applied at and removed from an outer circumferential portion of the endoscope head body laterally to the axis of the endoscope head body. The housing sheath part and the Albarran lever may form a common assembly which is separate from the endoscope head and can be treated as an individual unit. Hence, the Albarran lever provided on the housing sheath part is provided separately and detachably from the endoscope head body. The Albarran lever can be separated from the endoscope head body by the housing sheath part being removed from the endoscope head body.

In the endoscope head, the housing sheath part may be formed as an elastic housing sheath part which can be spread apart and can be completely separated from the endoscope head body, and which can include fastening means which fasten the housing sheath part to the outer circumferential portion of the endoscope head body. Thus, the assembly consisting of the housing sheath part and the Albarran lever can be easily attached to the endoscope head. The fastening means can be formed as engagement means. Protrusions capable of engaging in recesses formed on the outer circumferential portion of the endoscope head body may be formed as engagement means on the housing sheath part.

The housing sheath part may be formed as a hollow cylinder whose sheath includes an attachment opening extending along the cylinder extension direction and along the entire hollow cylinder. The hollow cylinder may be elastically spread apart at the attachment opening thereof and placed on the outer circumferential portion of the endoscope head body. Thus, the housing sheath part can be easily and quickly detached from the endoscope head body.

On the hollow cylinder, on the side opposite to the attachment opening, a tool opening may be formed, through which a tool can project laterally from the endoscope head body when the housing sheath part is placed on the endoscope head body. When the housing sheath part is attached to the endoscope head body, the endoscope is ready for operation. Tools can be advanced through the working channel to the Albarran lever which appropriately changes the lateral alignment of the tools. In the course of this, the tools project laterally from the endoscope head body through the tool opening of the housing sheath part.

The fastening means may be formed as a hinge member. The housing sheath part may comprise a hinge member which is hinged on the housing sheath part and is able to close the attachment opening. When the hinge member is closed, the housing sheath part can abut against the endoscope head body along the entire outer circumferential portion of the endoscope head body. In such a design, the housing sheath part is mounted to the endoscope head body in a fixed and stable manner. One side of the hinge member may be supported on the housing sheath part in a hinged manner and the opposite side of the hinge member may include a closing means, e.g. a nose, capable of engaging at the housing sheath part. Due to the elasticity of the housing sheath part, the housing sheath part can thus tightly abut against the endoscope head body in a correct position and with a predefined tension.

The housing sheath part may comprise a protrusion extending radially inward, on which the pivot axis of the Albarran lever is rotatably supported. Therefore, the housing sheath part is provided with the elements pivotally supporting the Albarran lever. The element (operating element) effecting the pivoting process of the Albarran lever may be provided in the endoscope head body.

The housing sheath part and the Albarran lever may be formed as a unit designed as a single-use product. For example, the housing sheath part and the Albarran lever can form a common assembly which is manufactured at low cost from plastic or any other suitable material. Thus, the common assembly consisting of the housing sheath part and the Albarran lever can be disposed of after a single use. When the endoscope is used again, a new assembly consisting of the housing sheath part and the Albarran lever is placed on the endoscope head body.

The endoscope head body may comprise a pivotable operating element which can be operated from the proximal side and with which the Albarran lever releasably engages when the housing sheath part is attached to the endoscope head body.

The endoscope head may comprise an ultrasonic head on the distal end of the endoscope head body and the portion of the endoscope head body where the Albarran lever can be applied at and removed from, may be situated proximally from the ultrasonic head. In this way, an endoscope can be provided which comprises an ultrasonic head on the distal end and includes, proximally from the ultrasonic head, an Albarran lever which is easily separable from the endoscope head.

In an alternative, an endoscope head according to the invention has been provided, the endoscope head comprising an ultrasonic head at the distal end and an Albarran lever arranged proximally from the ultrasonic head.

In a further alternative, an endoscope head according to the invention has been provided, the endoscope head comprising an ultrasonic head therein and an Albarran lever arranged distally from the ultrasonic head. In this further alternative, a working channel and a movement transmission channel are guided past the ultrasonic head.

In the endoscope head, the Albarran lever may be operated by means of a movement transmission mechanism, wherein the movement transmission mechanism in the endoscope head acts via a movement transmission channel and the movement transmission channel is sealed against the environment.

The movement transmission mechanism may be, for example, a pulling wire mechanism, a wire mechanism (pushing wire or pulling wire), a hydraulic mechanism or a pneumatic mechanism, transmitting a movement generated at a proximal control element (e.g. a joystick) via the movement transmission channel so as to actuate (pivot) the Albarran lever. In the case of the solution by means of the hydraulic mechanism or the pneumatic mechanism, the movement transmission channel is a simple channel which is sealed and filled with a movement transmission medium (hydraulic mechanism: e.g. water or another hydraulic medium; pneumatic mechanism: e.g. air).

Since the movement transmission channel and thus, the medium contained therein (hydraulic medium, air, pulling wire or wire, etc.) is sealed against the environment, it is avoided that germs and contaminations enter the movement transmission channel. Incidentally, the movement transmission channel and the Albarran lever are completely separated from each other.

Moreover, an Albarran lever holding member has been provided for an endoscope comprising an endoscope head in which at least one working channel is formed, wherein an Albarran lever capable of being pivoted is provided at the distal working channel end portion of the endoscope; the Albarran lever holding member including: a sheath element which can be placed on the endoscope head and in which the Albarran lever is pivotally supported.

The sheath element may be formed as a laterally open cylinder whose open side can be placed on the endoscope head, and the Albarran lever pivotally supported in the sheath element may include an opening adapted to be able to engage such that an operating element supported on the endoscope head can engage in the opening of the Albarran lever.

The Albarran lever holding member may be formed of plastic, for example, or any other suitable material. The Albarran lever holding member may be manufactured, for example, by means of a 3D-printer or an injection molding method. The sheath element and the Albarran lever can be manufactured separately and the Albarran lever can be installed in the sheath element in an assembly step.

The previously explained aspects of the present invention may be appropriately combined.

Figure 1:
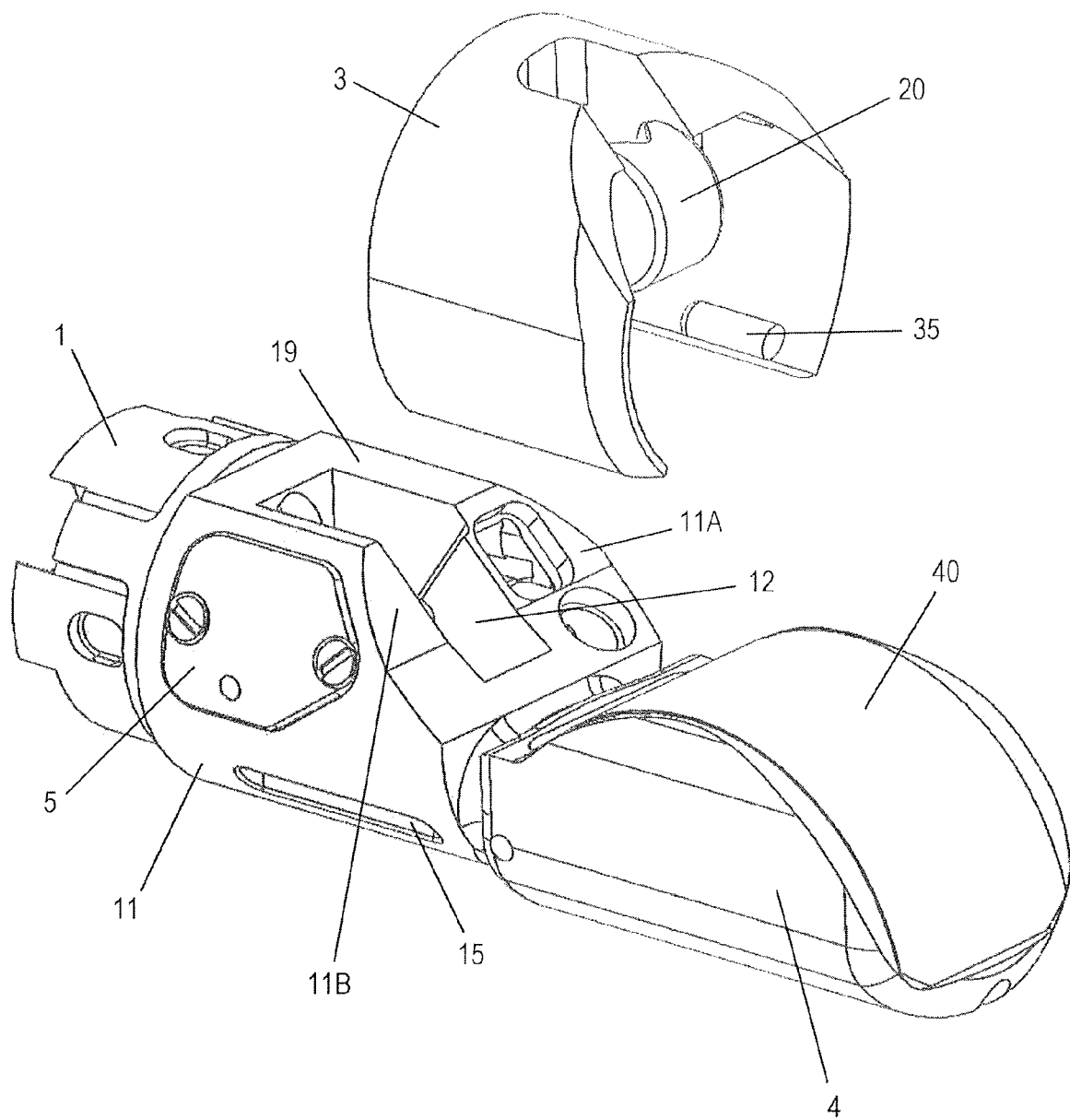
FIG. 1 shows a perspective view of an inventive endoscope head of a first embodiment in a disassembled state.

Below, the present invention is described in detail with reference to the drawings and based on the embodiments.

The endoscope head of the present invention can be used in the field of endoscopic ultrasound.

Endoscopic ultrasound (EUS) is a medical procedure in which endoscopy is combined with ultrasound to obtain images of the internal organs e.g. in the chest, abdomen and colon. EUS can be used to visualize the walls of these organs, or to look at adjacent structures. Combined with Doppler imaging, nearby blood vessels can also be evaluated.

Endoscopic ultrasonography is most commonly used in the upper digestive tract and in the respiratory system. For the patient, the procedure feels almost identical to the endoscopic procedure without the ultrasound part, unless ultrasound-guided biopsy of deeper structures is performed.

Ultrasound endoscopes are commonly used for diagnostic and therapeutic purposes in the upper gastroenterology area. The tools in use are penetrating the human tissue and are out of optical visibility, in that moment. In that case the ultrasound sensor still shows the way and location of the tools tip. Necessary tools can be controlled by the albarranlever of the respective endoscope. The physician observes e.g. either the stomach or the duodenum with the optical camera as well as taking pancreatic biopsy with support from the EUS sensors view.

In particular, for endoscopic ultrasound of the upper digestive tract, a probe is inserted into the esophagus, stomach, and duodenum during a esophagogastroduodenoscopy. Among other uses, it allows for screening for pancreatic cancer, esophageal cancer, and gastric cancer, as well as benign tumors of the upper gastrointestinal tract. It also allows for characterization and biopsy of any focal lesions found in the upper gastrointestinal tract, such as esophageal tuberculosis. Further, this procedure can also be used to identify malformations and masses in the bile ducts and pancreatic ducts.

Endoscopic ultrasound is performed with the patient sedated. The ultrasound endoscope is passed through the mouth and advanced through the esophagus to the suspicious area. From various positions between the esophagus and duodenum, organs within and outside the gastrointestinal tract can be imaged to see if they are abnormal, and they can be biopsied by a process called fine needle aspiration. Organs such as the liver, pancreas, and adrenal glands are easily biopsied, as are any abnormal lymph nodes. In addition, the gastrointestinal wall itself can be imaged to see if it is abnormally thick, suggesting inflammation or malignancy.

The technique is highly sensitive for detection of pancreatic cancer. With respect to pancreatic cancer, by endoscopic ultrasound local metastases can be detected.

However, in combination with a CT scan which provides information on regional metastases, endoscopic ultrasound provides an excellent imaging modality for diagnosis and staging of pancreatic carcinoma.

Endoscopic ultrasound can also be used in conjunction with endoscopic retrograde cholangio pancreatography. The ultrasound probe is used to locate gall stones which may have migrated into the common bile duct.

Endoscopic ultrasound can also be used for imaging of the rectum and colon, although these applications are lesser known. Endoscopic ultrasound can be used primarily to stage newly diagnosed rectal or anal cancer. EUS-guided fine needle aspiration may be used to sample lymph nodes during this procedure. Evaluation of the integrity of the anal sphincters may also be done during lower EUS procedures.

An endoscopic ultrasound probe placed in the esophagus can also be used to visualize lymph nodes in the chest surrounding the airways (bronchi), which is important for the staging of lung cancer. Ultrasound can also be performed with an endoscopic probe inside the bronchi themselves, a technique known as endobronchial ultrasound.

EMBODIMENT 1

First of all, a first embodiment of the present invention is described with reference to FIGS. 1 to 8.

Figure 2:
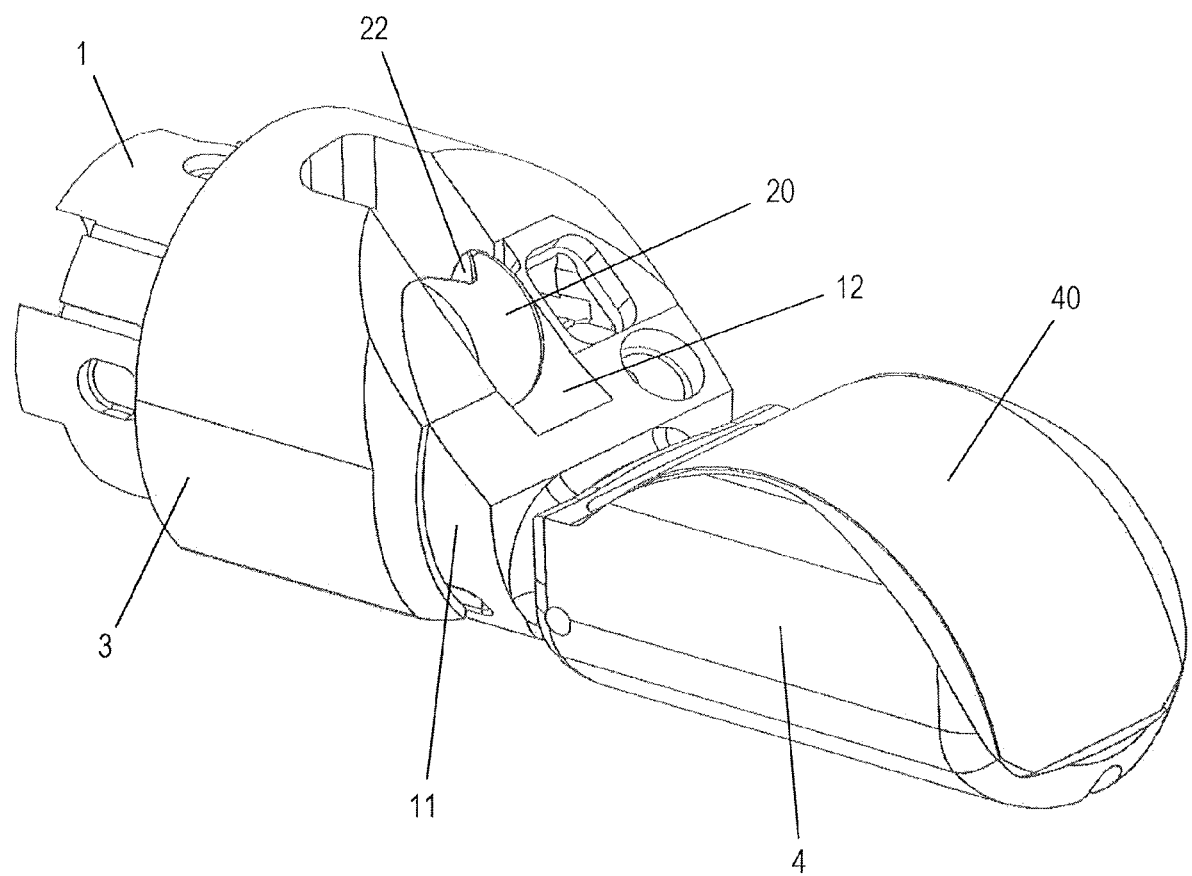
FIG. 2 shows a perspective view of the inventive endoscope head of the first embodiment in the assembled state.

FIGS. 1 and 2 both show a perspective view of a first embodiment of an endoscope head 1 according to the invention. More precisely, FIG. 1 shows a disassembled state of the endoscope head 1 and FIG. 2 shows the assembled state.

The endoscope head 1 shown in the Figures forms part of an endoscope according to the invention. This endoscope may be formed as a flexible endoscope for the gastrointestinal tract. The endoscope comprises an operation unit and an insertion portion. The operation unit is positioned on the proximal side and the insertion portion is positioned on the distal side of the endoscope.

The operation unit (not shown in the drawings) comprises an actuating lever (such as a joystick or a simple lever arm, for example) for actuating an Albarran lever, a working channel inlet and an adjusting knob for bending a bending portion of the endoscope. The operation unit is connected to a video processor, a light source device, a display device and the like.

The insertion portion is a long tube-like element. The proximal end of the insertion portion is connected with the operation unit. The insertion portion comprises, in this order seen from the operation unit, a flexible portion, the bending portion and a cap. The flexible portion is elastic. The bending portion is bent as a reaction to an actuation of the adjusting knob. A rigid end piece portion is formed on the distal end of the bending portion. The rigid end piece portion forms the so-called endoscope head.

The inventive endoscope head 1 of FIGS. 1 and 2 comprises a longitudinal endoscope head body 11 and a subsequently further described housing sheath part 3 including a subsequently further described Albarran lever 20.

The endoscope head body 11 is constructed in a cylinder-like manner and, on the distal side thereof, provided with an ultrasonic head chamber 4 in which an ultrasonic head 40 is installed. On its proximal side, the endoscope head body 11 is connected to an operation unit (not shown) via a cable (not shown) or without a cable. The operation unit is used to control the endoscope head 1.

The endoscope head body 11 comprises a working channel 13 and a pulling wire channel 14 (see FIG. 7), both extending along the longitudinal direction of the endoscope head body 11 and parallel to each other. The pulling wire channel 14 contains a subsequently described pulling wire for actuating the subsequently described Albarran lever 20. The working channel 13 guides micro tools for examining e.g. the esophagus or the duodenum, the bile duct, the gall bladder, the pancreatic duct, the pancreas, etc. The Albarran lever 20 which is described below and able to change the lateral alignment of the micro tools in the known manner is arranged at the outlet of the working channel 13. In other words, the Albarran lever 20 changes the alignment angle of the micro tools advanced through the working channel 13 in parallel to the axis of the endoscope head 1. The alignment of the micro tools is then changed to a lateral direction by means of the Albarran lever 20, the micro tools then project laterally from the endoscope head so as to be advanced in a bile duct, for example.

The shape and the deflection angle of the Albarran lever are not restricted in the present invention.

Figure 5:
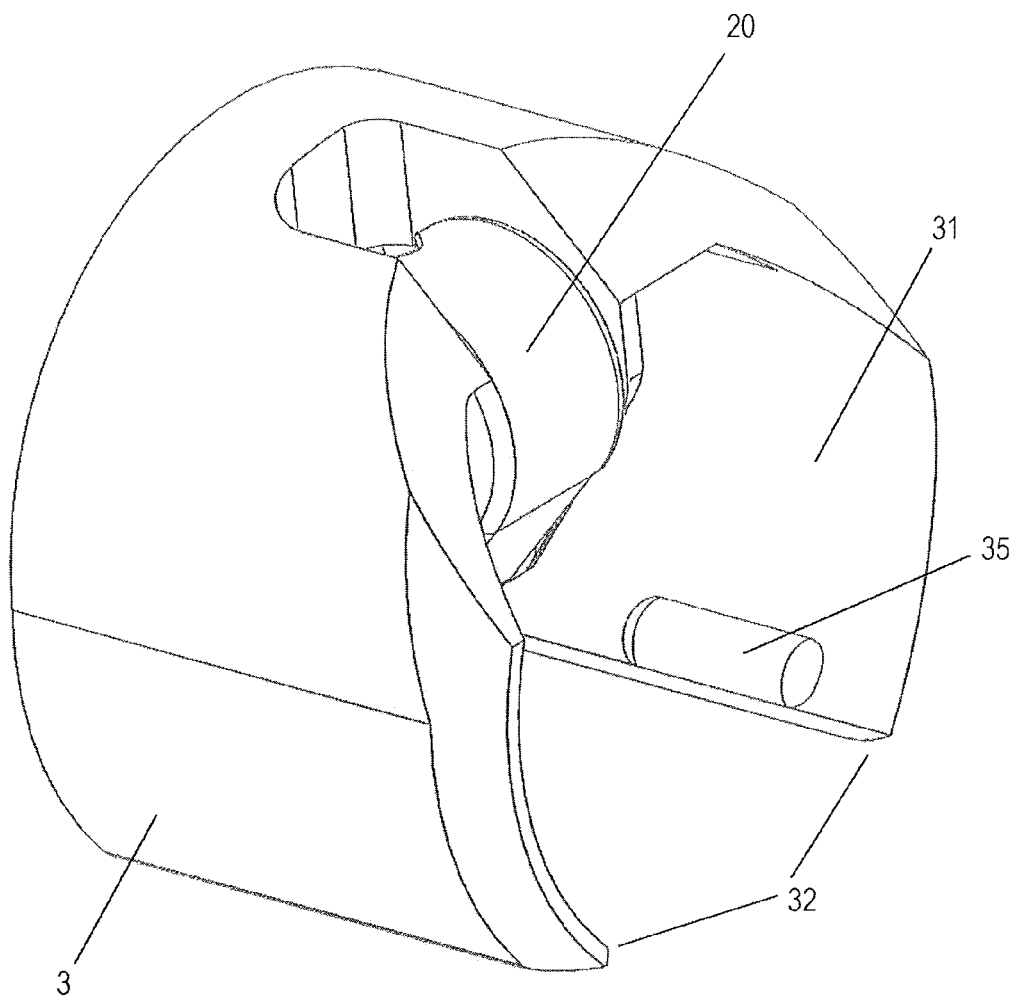
FIG. 5 shows a further perspective view of a housing sheath part of the inventive endoscope head of the first embodiment.

As shown in FIGS. 1, 2 and 5, the endoscope head body 11 comprises an Albarran lever chamber 12 extending in the embodiment from a region near the longitudinal axis of the endoscope head body 11 in the radial direction. In other words, the Albarran lever chamber 12 is open in the radial direction. Moreover, the Albarran lever chamber 12 extends in the axial direction of the endoscope head body 11. On the proximal side of the Albarran lever chamber 12, the working channel 13 enters into the Albarran lever chamber 12. On the distal side of the Albarran lever chamber 12, the ultrasonic head chamber 4 is provided.

The endoscope head body 11 comprises two lateral extension portions 11A and 11B which are formed as side walls or side portions and are adjacent to the Albarran lever chamber 12. More precisely, as is shown in FIGS. 1, 2 and 6 to 8, the endoscope head body 11 includes a first side portion 11A for a camera and an illumination means, and a second side portion 11B for a pulling wire.

A camera 17 and an illumination means 18, aligned laterally upwards in FIGS. 1, 2 and 6 to 8, are installed in the first side portion 11A. The direction in which the camera 17 and the illumination means 18 are aligned is defined as the viewing direction. In the embodiment, the illumination means 18 is positioned on the distal end of the first side portion 11A and the camera 17 is provided proximally to the illumination means 18. Thus, the supply lines and signal lines for the camera 17 and the illumination means 18 can be arranged inside the first side portion 11A. These supply lines and signal lines extend toward the operation unit.

As is described below in further detail, a pulling wire channel 14 as a movement transmission channel, a pulling wire end and a pivot lever 6 are accommodated in the second side portion 11B.

On the side directed to the viewing direction, the first side portion 11A and the second side portion 11B are formed in a flat manner such that a flattening 19 of the endoscope head body 11 is provided. The flattening 19 of the endoscope head body 11 is a plane surface facing toward the viewing direction. In the embodiment, the camera 17 and the illumination means 18 are arranged distally to the flattening 19.

Thus, the Albarran lever chamber 12 is sandwiched between and laterally delimited by the first side portion 11A and the second side portion 11B. The limitation walls of the first side portion 11A and the second side portion 11B extend in an approximately radial direction in parallel to each other. Thus, the Albarran lever chamber 12 in the embodiment has a cuboid shape. The limitation walls of the first side portion 11A and the second side portion 11B are perpendicular to the flattening 19.

An accommodation chamber 11B1 is formed in the second side portion 11B. On the distal side, on the proximal side, on the side facing towards the Albarran lever chamber 12, on the side facing towards the viewing direction and on the side opposed to the viewing direction, the accommodation chamber 11B1 is surrounded by the second side portion 11B and is open only on the side opposed to the Albarran lever chamber 12. The pulling wire channel 14, in which a pulling wire (control wire, not shown) is guided, opens out on the proximal side of the accommodation chamber 11B1. The pulling wire (control wire) extends up to the operation unit and is actuated by the actuating lever for actuating an Albarran lever.

A pivot lever 6 is rotatably supported in the accommodation chamber 11B1. More precisely, a bearing bore (passage bore) 11B2 extends through the wall of the accommodation chamber 11B1, which is provided on the side facing towards the Albarran lever chamber 12. This bearing bore 11B2 connects the accommodation chamber 11B1 with the Albarran lever chamber 12. The pivot lever rotating shaft 62 of the pivot lever 6 is rotatably supported in the bearing bore 11B2. The pivot lever rotating shaft 62 protrudes on both sides of the bearing bore 11B2, i.e. on the side of the accommodation chamber 11B1 and on the side of the Albarran lever chamber 12. The pivot lever rotating shaft 62 is installed in a sealed manner in the bearing bore 11B2. Thus, the accommodation chamber is (watertightly) sealed against the Albarran lever chamber 12. The pivot lever rotating shaft 62 is formed perpendicularly to the pivot lever 6 and integrally with the pivot lever 6 on an end portion of the pivot lever 6. The pivot lever rotating shaft 62 and the pivot lever 6 may be formed as one body or may be separate components which are connected with each other in a form-fitting or force-fitting manner. The pivot lever 6 has a pulling wire nipple accommodation 63 on the end portion opposed to the pivot lever rotating shaft 62. The pulling wire nipple accommodation 63 may be molded to the pivot lever 6 or fixed to the pivot lever 6 as a separate body. The distal pulling wire end of the pulling wire is hooked in or fitted in the pulling wire nipple accommodation 63 or otherwise fixed thereto.

The open side of the accommodation chamber 11B1, i.e. the side of the accommodation chamber 11B1 opposed to the Albarran lever chamber 12, is closed by a cover member 5. The cover member 5 is a flat plate member adapted to the outer contour of the endoscope head body 11 and has a suitable size completely covering the open side of the accommodation chamber 11B1. The cover member 5 covers the open side of the accommodation chamber 11B1 in such a manner that the open side of the accommodation chamber 11B1 is (watertightly) sealed. For example, the cover member 5 is screwed to the outer circumference of the endoscope head body 11 by means of two screws so as to cover the accommodation chamber 11B1, as it is shown in FIG. 1. Thus, the accommodation chamber 11B1, except for the pulling wire channel, is completely sealed. In other words, the pulling wire channel is completely sealed against the environment (in a watertight manner).

On the end of the pivot lever rotating shaft 62, arranged in the Albarran lever chamber 12, the pin 16 formed as a round rod body is arranged as an operating element. The pin 16 extends from the pivot lever rotating shaft 62 approximately in parallel to the pivot lever 6. However, the pin 16 may also extend from the pivot lever rotating shaft 62 at a predetermined angle offset with respect to the pivot lever 6 in the proximal or the distal direction. The relative extension direction of the pin 16 and the pivot lever 6 is not restricted in the invention and can be appropriately selected.

Thus, the pin 16 can be actuated by means of the actuating lever of the operation unit by pulling the pulling wire via the actuating lever; this causes the pulling wire nipple accommodation 63 to be pivoted about the pivot lever rotating shaft 62 as rotation point and the pin 16 to be rotated about the same angular extent.

An Albarran lever described in the following can be placed on the pin 16.

An ultrasonic head chamber 4 is arranged on the distal side of the endoscope head body 11. The ultrasonic head chamber 4 may be constructed in any suitable manner and holds the ultrasonic head 40 therein such that the ultrasonic head 40 is at least aligned to the viewing direction. The ultrasonic head 40 is capable of transmitting and receiving ultrasonic signals in the viewing direction. Ideally, the ultrasonic head 40 is configured such that it is capable of transmitting and receiving ultrasonic signals in and from directions which are not limited to the viewing direction alone.

The ultrasonic head chamber 4 may be mounted on the distal side of the endoscope head body 11 or form an integral unit with the endoscope head body 11. Alternatively, the ultrasonic head chamber 4 may be dismounted on the distal side of the endoscope head body 11.

As it is shown in FIG. 1, grooves 15 extending in the axial direction of the endoscope head body 11 are provided on the endoscope head body 11. More precisely, a first groove 15 is formed on the first side portion 11A below the accommodation chamber 11B1 (i.e. on the side opposed to the flattening 19) on the outer circumferential surface of the endoscope head body 11.

A second groove 15 is provided on the second side portion 11B on the same level as the first groove 15 and parallel to the first groove 15. The second groove 15 is not visible in the drawings since it is positioned on the side of the endoscope head body 11, which faces away from the viewer.

The first groove 15 and the second groove 15 are formed as longitudinal recesses or depressions.

The housing sheath part 3 comprises a sheath 31 having a hollow cylinder-like shape. The inner contour of the sheath 31 of the housing sheath part 3 is adapted to the outer contour of the endoscope head body 11. More precisely, the hollow cylinder shape of the sheath 31 is open on one cylinder sheath side. Thus, the sheath 31 includes two lateral extensions which are elastic. The cylinder sheath side of the sheath 31 is open between the ends of the lateral extensions. The sheath 31 is elastic and can be bent open on the lateral extensions thereof. Thus, an attachment opening 32 is provided between the ends of the lateral extensions. Since the housing sheath part 3 is elastic, the attachment opening 32 can be expanded by bending open the sheath ends adjacent to the attachment opening 32. When the lateral extensions of the sheath 31 are bent open, the housing sheath part 3 can be placed on the endoscope head body 11 by inserting the endoscope head body 11 quasi through the attachment opening 32 into the sheath 31, see FIGS. 1 and 2.

On the circumferential side opposed to the attachment opening 32, the housing sheath part 3 has a tool opening 33 extending in the axial direction of the housing sheath part 3. When the housing sheath part 3 is placed on the endoscope head body 11, the tool opening 33 is arranged exactly above the Albarran lever chamber 12. The size (in particular the width) of the tool opening 33 is adapted to the Albarran lever chamber 12.

Figure 3:
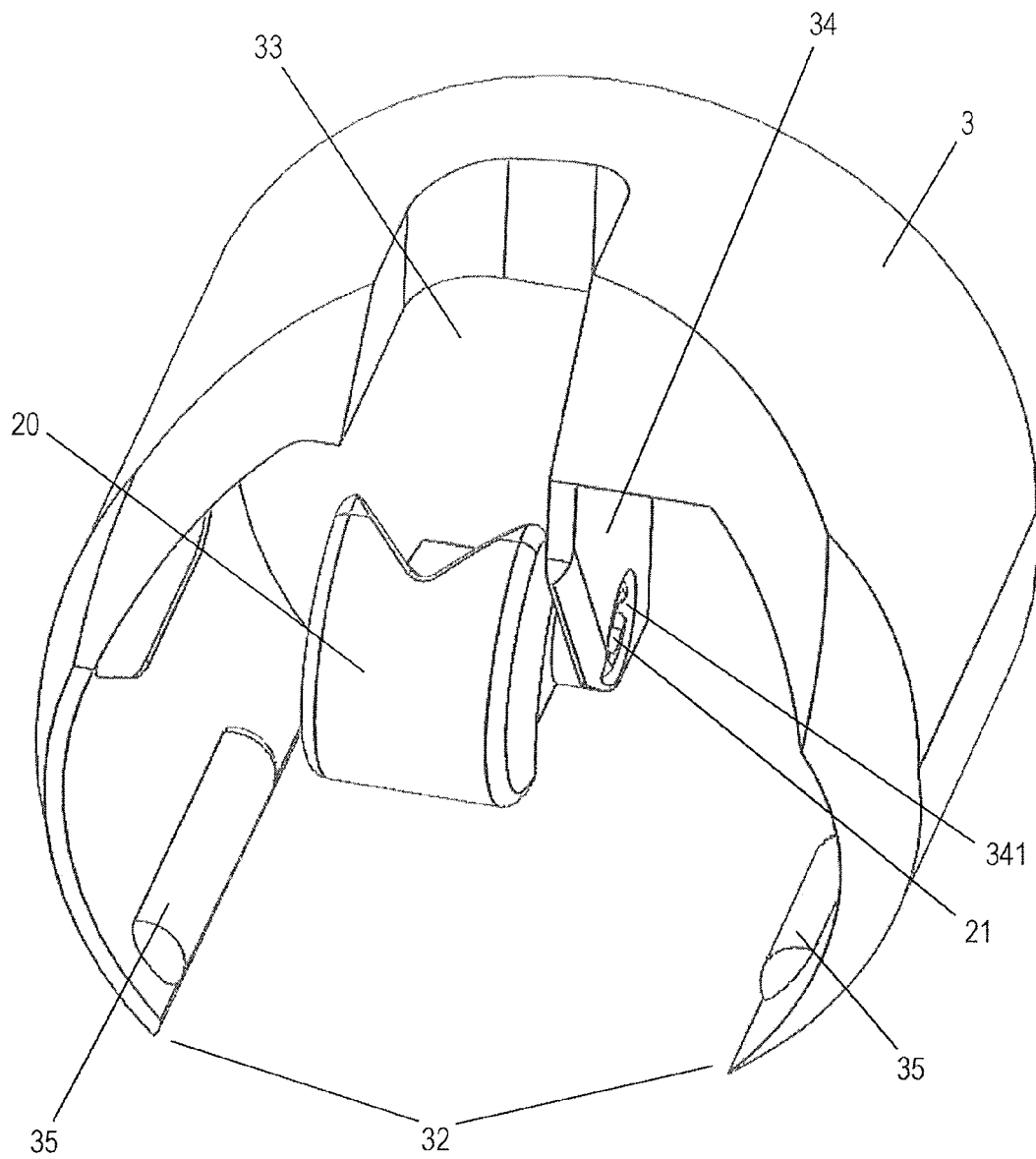
FIG. 3 shows a perspective view of a housing sheath part of the inventive endoscope head of the first embodiment.
Figure 4:
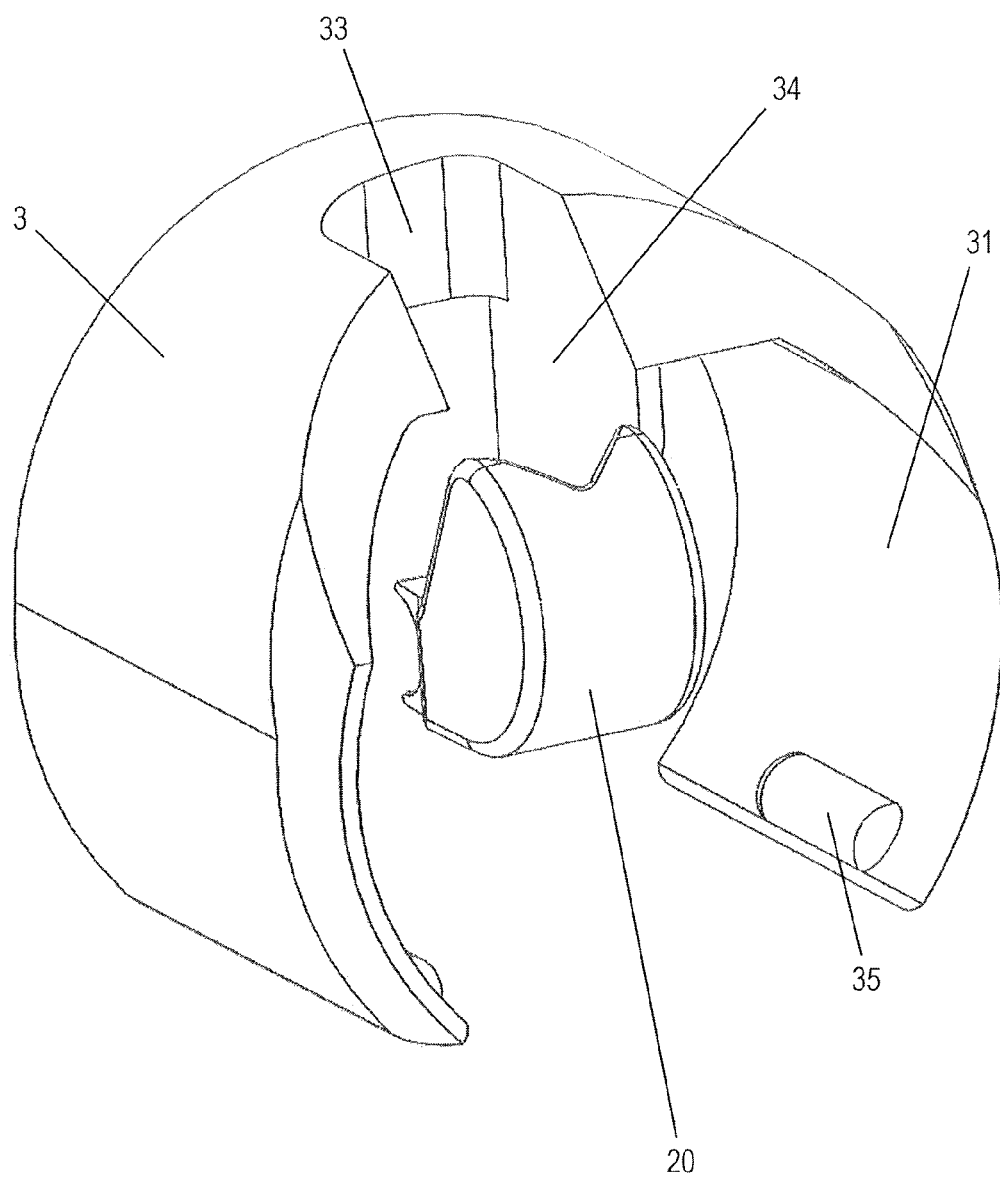
FIG. 4 shows a further perspective view of a housing sheath part of the inventive endoscope head of the first embodiment.

On the lateral extensions of the sheath 31, on the end portion opposed to the tool opening 33, ribs 35 are formed adjacent to the attachment opening 32, as this is shown in FIGS. 3 to 5. Each rib 35 extends in the axial direction of the housing sheath part 3. When the housing sheath part 3 is placed on the endoscope head body 11, the ribs 35 engage in the grooves 15. The shape and size of the ribs 35 is suitably adapted to the shape and size of the grooves 15.

On the inner circumferential side, adjacent to the tool opening 33, the housing sheath part 3 has a housing sheath flattening adapted to the flattening 19. In this region adjacent to the tool opening 33, the housing sheath flattening is provided with a thicker wall thickness than the rest of the sheath 31. When the housing sheath part 3 is placed on the endoscope head body 11, the housing sheath flattening abuts against the flattening 19. On an axial side of the tool opening 33, a protrusion 34 is formed on the housing sheath flattening. The protrusion 34 extends radially inwards in the housing sheath part 3, perpendicular to the housing sheath flattening. The protrusion 34 forms an Albarran lever holder. The protrusion 34 is formed to be flat and projects into the Albarran lever chamber 12 when the housing sheath part 3 is arranged on the endoscope head body 11.

On the end portion opposed to the housing sheath flattening, the protrusion 34 has a passage bore 341 formed perpendicular to the extension direction of the protrusion 34 and perpendicular to the axis of the housing sheath part 3. An Albarran lever shaft 21 is rotatably supported in the passage bore 341. The Albarran lever shaft 21 protrudes laterally from the Albarran lever 20, as it is shown in FIG. 3. Thus, the Albarran lever 20 is rotatably supported on the radially inner end portion of the protrusion 34.

The Albarran lever 20 has an insertion bore which is not shown in the drawings and in which the previously described pin 16 is inserted. The inner diameter of the insertion bore of the Albarran lever 20 is adapted to the outer diameter of the pin 16, such that a smooth relative displacement between the pin 16 and the insertion bore of the Albarran lever 20 is realized.

When the housing sheath part 3 is placed on the endoscope head body 11, the Albarran lever 20 is slid on the pin 16. In other words, in this position the pin 16 engages in the Albarran lever 20 and can pivot the Albarran lever. Thus, the Albarran lever 20 can be applied (inserted) on the endoscope head body 11 laterally to the axis of the endoscope head body 11 and, in turn, removed from the endoscope head body 11 laterally to the axis of the endoscope head body 11.

When the housing sheath part 3 is placed on the endoscope head body 11, the Albarran lever shaft 21 is arranged at a position which forms an imagined extension to the pivot lever rotating shaft 62.

The Albarran lever 20 may have any suitable shape and includes a tool pushing surface 22. By means of the tool pushing surface 22, tools guided through the working channel 13 can be pushed to the lateral side of the endoscope head body 11 in the known manner. In the installed state of the Albarran lever 20, the tool pushing surface 22 is positioned opposite to the orifice of the working channel 13 into the Albarran lever chamber 12.

Figure 6:
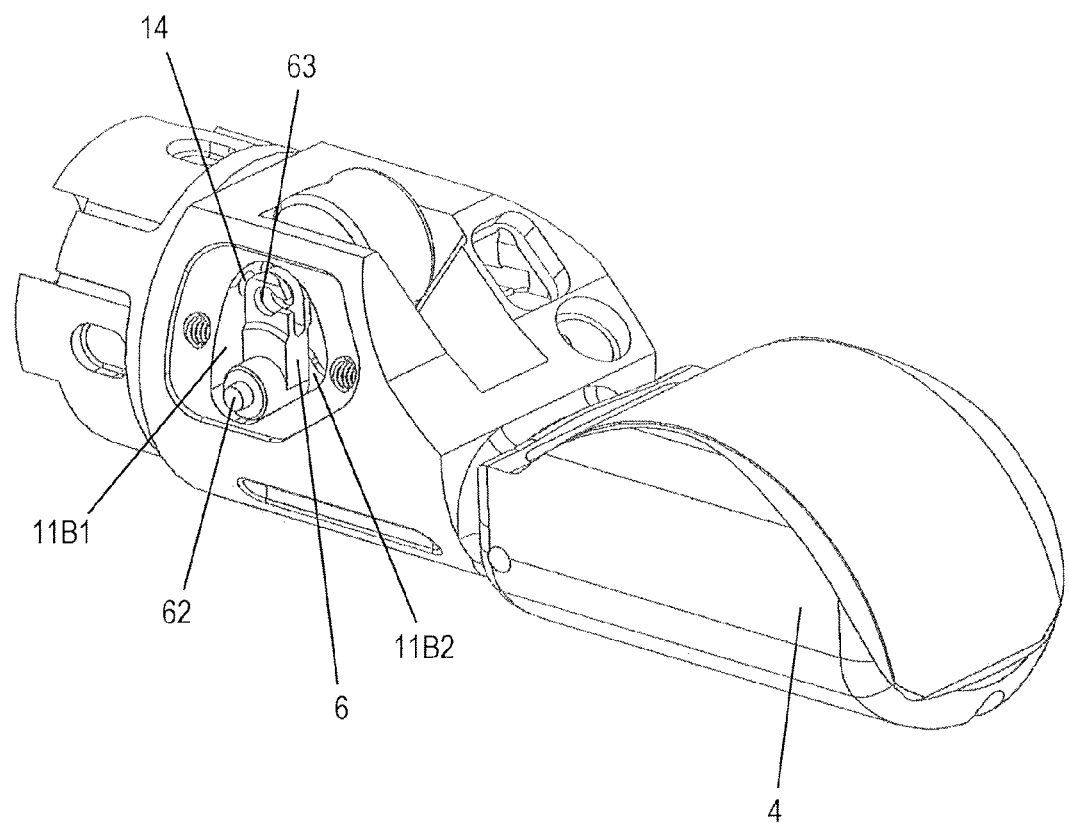
FIG. 6 shows a perspective view of an endoscope head body of the endoscope head of the first embodiment with an Albarran lever being in a non-pivoted state.
Figure 7:
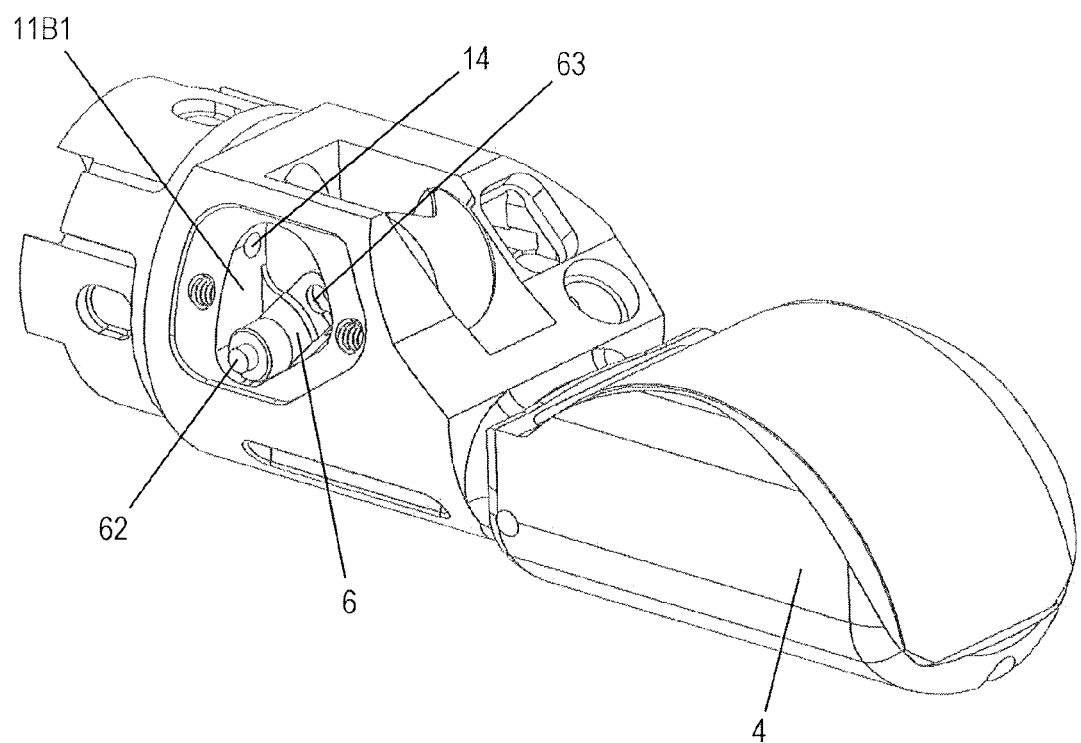
FIG. 7 shows a perspective view of the endoscope head body of the endoscope head of the first embodiment with the Albarran lever being in a pivoted state.
Figure 8:
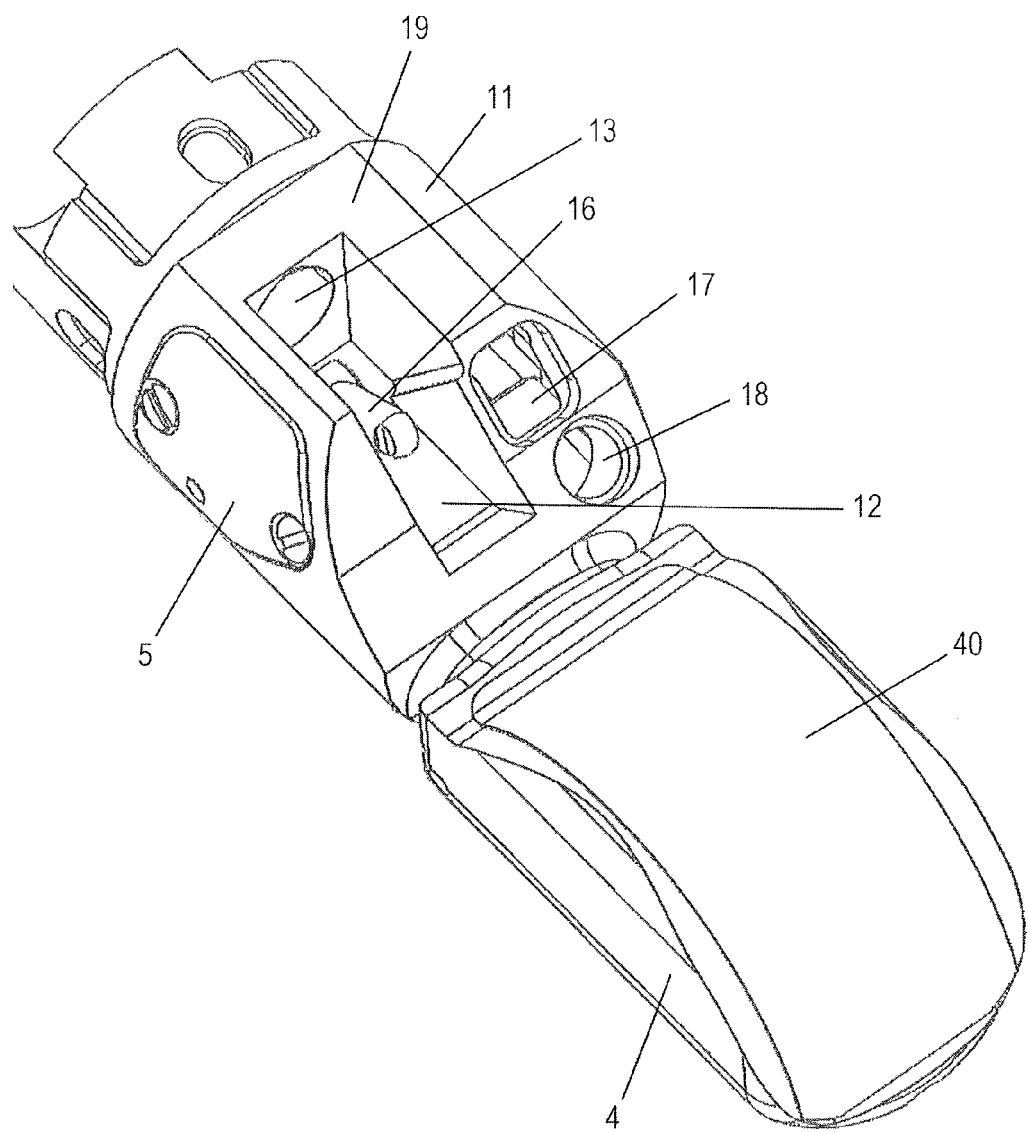
FIG. 8 shows a perspective view of the endoscope head of the first embodiment obliquely from above, without the housing sheath part.
Figure 9:
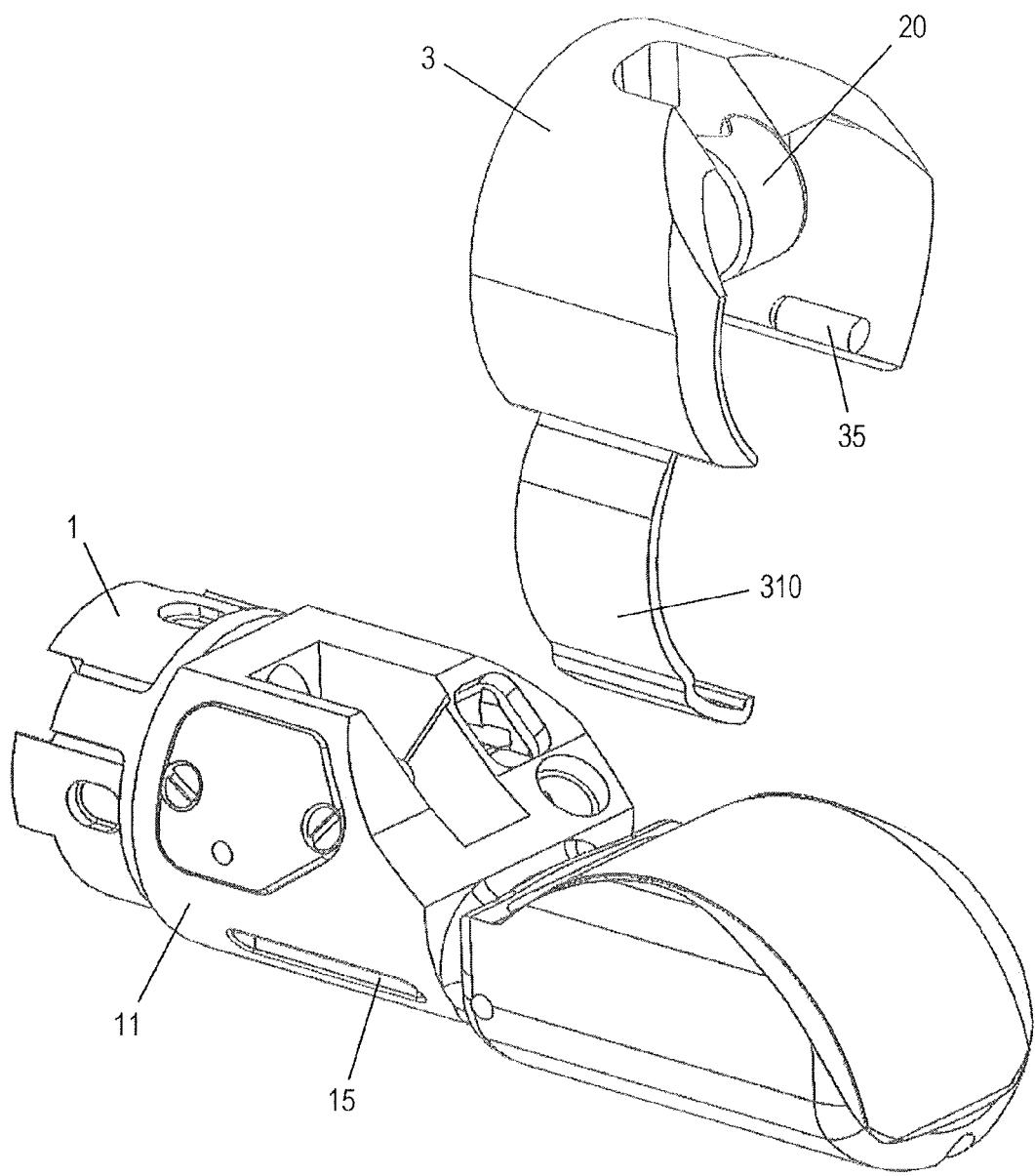
FIG. 9 shows a perspective view of an inventive endoscope head of a second embodiment in a disassembled state.
Figure 10:
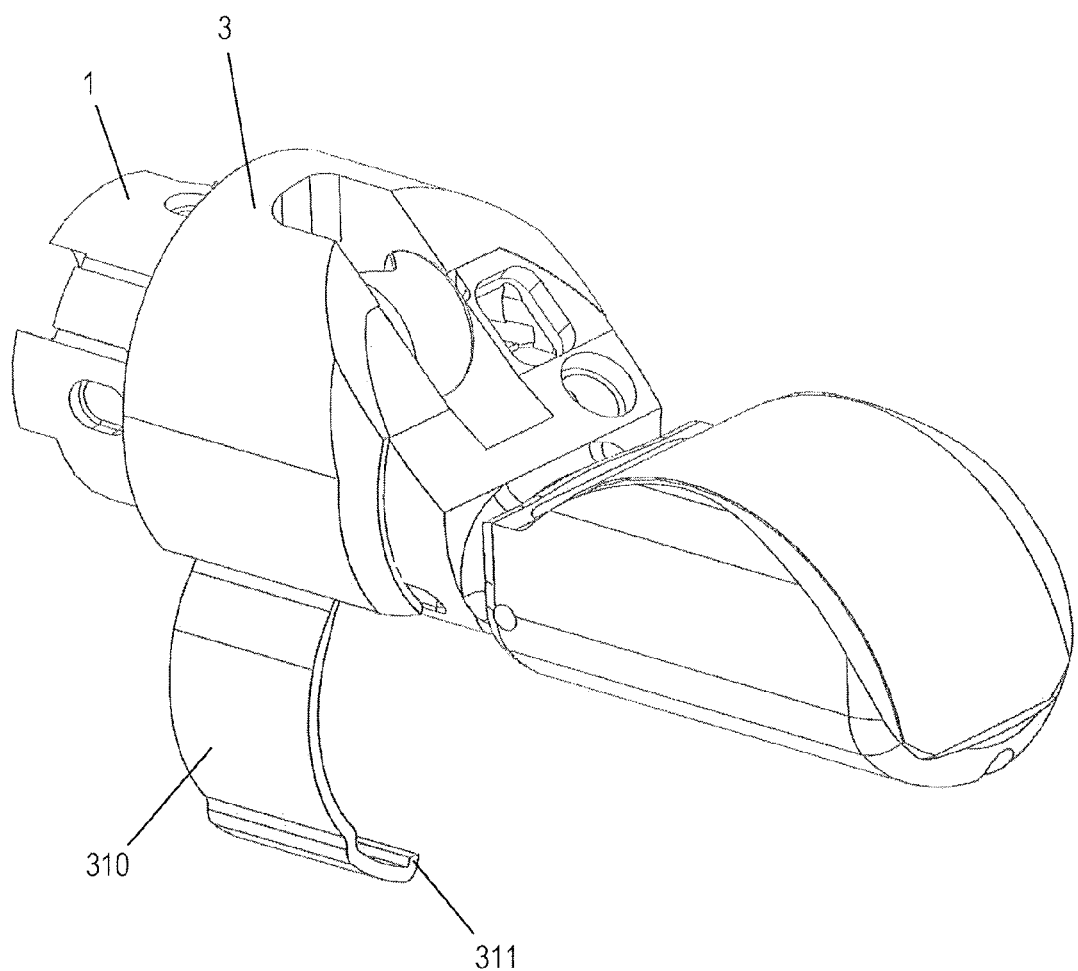
FIG. 10 shows a perspective view of the inventive endoscope head of the second embodiment, with a housing sheath part being placed on the endoscope head.
Figure 11:
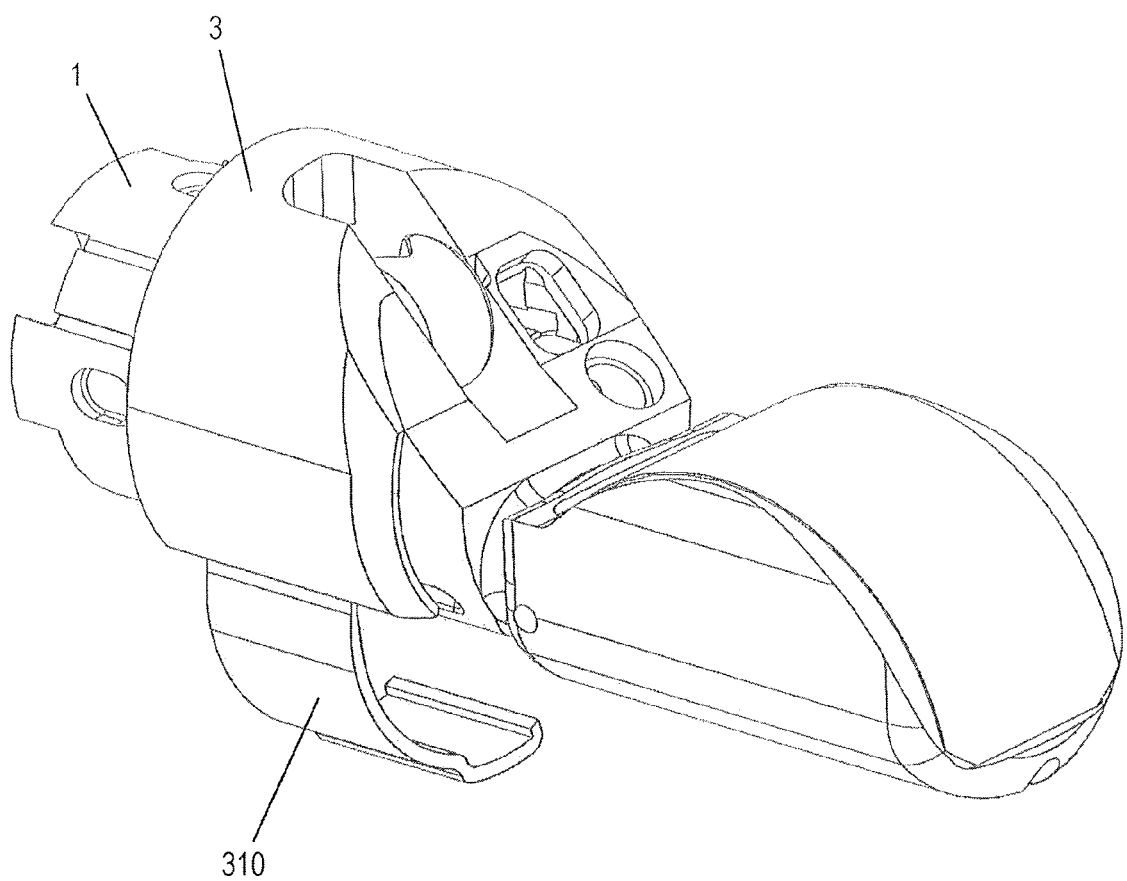
FIG. 11 shows a perspective view of the inventive endoscope head of the second embodiment, with a hinge member of the housing sheath part being closed.
Figure 12:
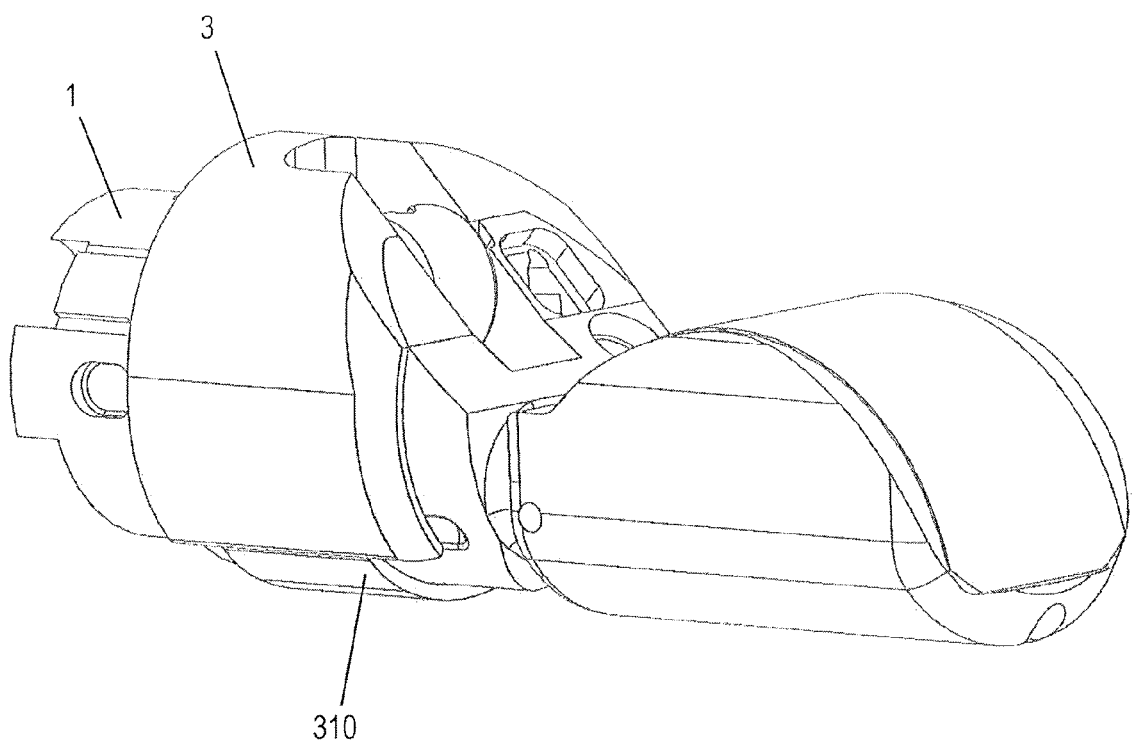
FIG. 12 shows a perspective view of the inventive endoscope head of the second embodiment with the hinge member of the housing sheath part on the endoscope head being closed.
Figure 13:
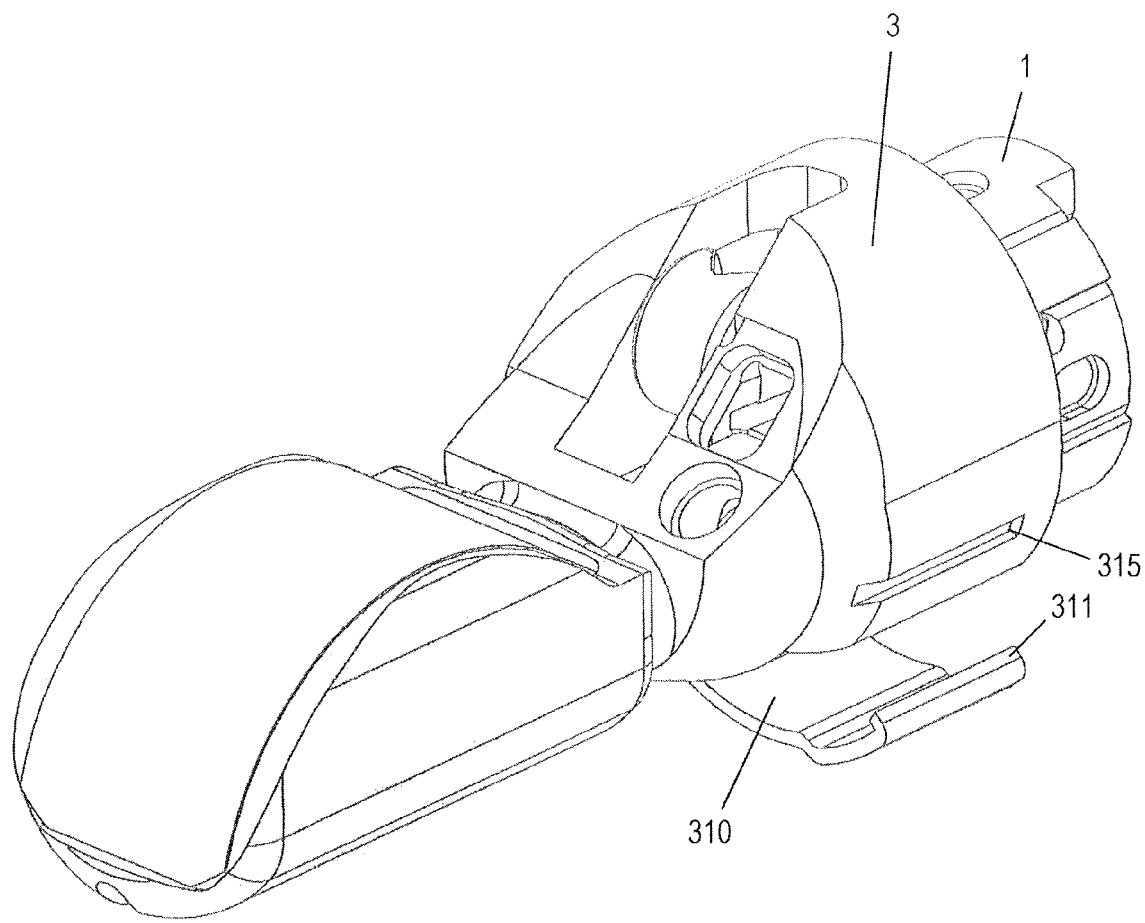
FIG. 13 shows a perspective view of the inventive endoscope head of the second embodiment, with a hinge member of the housing sheath part being closed.

The Albarran lever 20 can be slid on the pin 16 such that it extends approximately parallel to the pivot lever 6, as it is shown in FIGS. 6 and 7. Thus, in a state when the housing sheath part 3 is placed on the endoscope head body 11, there are two end positions for the position of the Albarran lever 20. FIG. 6 shows the Albarran lever 20 in a non-pivoted state with the pulling wire being released. FIG. 7 shows the Albarran lever 20 in a pivoted state with the pulling wire being pulled.

The housing sheath part 3 and the Albarran lever 20 form a common assembly. The housing sheath part 3 and the Albarran lever 20 are each made of plastic or any other cost-efficient material. They can be cost-efficiently manufactured by means of injection molding or a 3D-printer. Thus, the assembly consisting of the housing sheath part 3 and the Albarran lever 20 is suitable for single use. After the use, the assembly consisting of the housing sheath part 3 and the Albarran lever 20 can be disposed of. The endoscope itself comprising the endoscope head body 11 according to the invention includes hardly any undercuts and is therefore easy to clean. The Albarran lever 20, on the other hand, includes undercuts and is more difficult to clean. Germs and contaminations might remain stuck to locations of the Albarran lever that are difficult to access. In the present invention, this problem is solved by designing the assembly consisting of the housing sheath part 3 and the Albarran lever 20 such that it is replaceable. For the next application, the cleaned and sterilized endoscope is provided with a new assembly of housing sheath part 3 and Albarran lever 20. In this way, the endoscope can be cost-effectively used again after an application, namely free of germs and contaminations.

The Albarran lever is completely separated from the pulling wire. Due to this construction, the pulling wire channel is sealed, with the pulling wire being completely sealed against the environment. The sealing of the pulling wire channel and the pulling wire is watertight.

Preferably, the housing sheath part as an Albarran lever holding member and the Albarran lever are made of plastic by means of a 3D-printer or injection molding, for example. By the manufacturing by means of a 3D-printer or injection molding, the housing sheath part and the Albarran lever can be manufactured accurately, but still at low cost. Other appropriate manufacturing methods may be applied as long as they allow for an accurate and cost-efficient production. Preferably, the housing sheath part and the Albarran lever are manufactured separately and then put together as an assembly for the purpose of a single use. In a molding step, the housing sheath part as sheath element and the Albarran lever are separately manufactured and in an assembly step, the Albarran lever is installed in the housing sheath part.

EMBODIMENT 2

In the following, a second embodiment of the present invention is described with reference to FIGS. 9 to 13.

In the first embodiment, the housing sheath part 3 is engaged at the endoscope head body 11 by the ribs 35 engaging in the grooves 15. Thus, in the first embodiment, the ribs 35 and the grooves 15 represent the fastening means by which the housing sheath part 3 is attached to the endoscope head body 11.

In the second embodiment, the endoscope head 1 of the first embodiment and a housing sheath part 3 modified compared to the housing sheath part 3 of the first embodiment, are applied. Therefore, only those aspects in which the second embodiment differs from the first embodiment are described in the following.

In the second embodiment, another (additional) fastening means in the shape of a hinge member 310 is provided on the housing sheath part 3. The hinge member 310 bridges over the attachment opening 32. One side of the hinge member 310 is supported in a hinged manner on the housing sheath part 3 in an edge region of the attachment opening 32. The opposite side of the hinge member 310 includes a closing means, such as a nose 311, capable of engaging in an engagement groove 315 on the opposite edge region of the attachment opening 32 at the housing sheath part 3.

The hinge mechanism of the hinge member 310 on the housing sheath part 3 may be formed as a film hinge. More precisely, the hinge member 310 is integrally provided on the housing sheath part 3 as a thin-walled connection (e.g. in the shape of a fold). Due to its flexibility, the thin-walled connection enables a rotational movement of the hinge member 310 on the housing sheath part 3. Manufacturing the film hinge is extremely cost-effective.

Apart from that, the housing sheath part 3 corresponds to the housing sheath part 3 of the first embodiment.

EMBODIMENT 3

Figure 14:
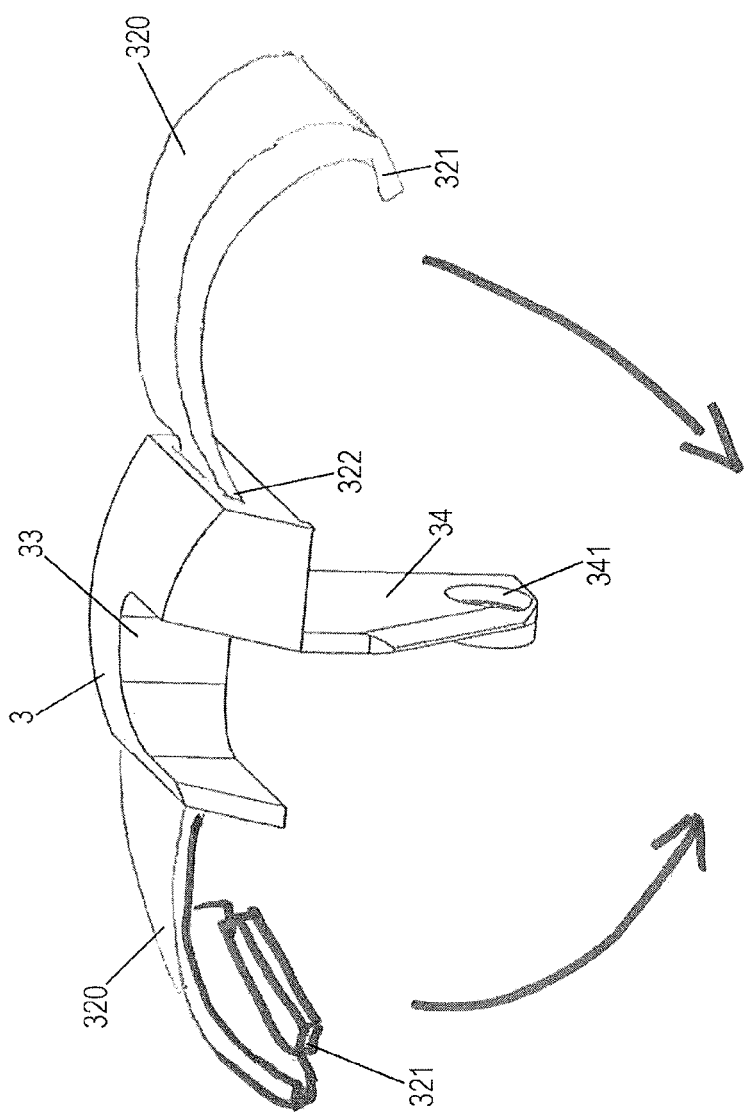
FIG. 14 shows a perspective view of an inventive housing sheath part of a third embodiment.

FIG. 14 shows a perspective view of an inventive housing sheath part of a third embodiment.

In the third embodiment, the endoscope head 1 of the first embodiment and a housing sheath part 3 modified compared to the housing sheath part 3 of the first embodiment are applied. In the first embodiment, the housing sheath part 3, in the region of the housing sheath flattening adjacent to the tool opening 33, has a thicker wall thickness than the rest of the sheath 31.

In the third embodiment, a housing sheath part 3 also includes the region of the housing sheath flattening, which is adjacent to the tool opening 33, as it is shown in FIG. 14. However, the housing sheath part 3 does not include the two lateral extensions of the first embodiment which comprise the ribs 35 and the ends of which define the attachment opening 32. As opposed to the first embodiment, the housing sheath part 3 in the third embodiment includes only that portion of the housing sheath flattening which is adjacent to the tool opening 33. On each of the lateral sides of the portion of the housing sheath flattening, the housing sheath part 3 is provided with a fastening means in the shape of a hinge member 320. One side of the hinge member 320 is, on an edge region of the portion of the housing sheath flattening, supported on the housing sheath part 3 via a hinge mechanism 322. The opposite side of the hinge member 320 includes a closing means such as a nose 321 which can engage at the endoscope head body in an engagement groove provided for this purpose.

The hinge mechanism of the two hinge members 320 on the housing sheath part 3 may be designed as a film hinge 322. More precisely, each of the hinge members 320 is integrally provided on the housing sheath part 3 in the shape of a thin-walled connection as a film hinge 322 (e.g. as a fold). Due to its flexibility, the thin-walled connection of the film hinge 322 enables a rotational movement of the hinge member 320 on the housing sheath part 3. The manufacture of the film hinge 322 is extremely cost-effective.

Alternatives

In embodiment 1, the rib 35 is provided as a fastening means which is formed at the housing sheath part 3 and engages with the groove 15 of the endoscope head body 11. Adjacent to the attachment opening 32, a right and a left rib 35 is provided, each being parallel to the extension direction of the endoscope head body 11. The invention is not restricted thereto. Instead of the rib 35, one or more pin-like protrusions may be formed on the housing sheath part 3, which respectively engage in one or more hole-like recesses on the endoscope head body 11 instead of the groove 15. Any type of fastening means is possible, as long as the same ensures that the housing sheath part 3 is securely held in place at the endoscope head body 11. Thus, as a matter of fact, the rib 35 may also be formed on the endoscope head body 11 and the groove 15 acting together with the rib 35 may be formed on the housing sheath part 3. Further, screws by which the housing sheath part is screwed to the endoscope head body may be used as fastening means. "Fastening means" thus refers to any releasable fastening means.

In embodiment 1, the region of the housing sheath flattening on the housing sheath part 3 is formed such that the wall thickness of the housing sheath part 3 is reinforced (see the drawings). Thereby, the housing sheath part 3 becomes more rigid and more stable. The invention is not restricted thereto. The wall thickness of the housing sheath part 3 may also be uniform.

In embodiment 1, a protrusion 34 is shown as Albarran lever holder. The protrusion 34 extends approximately radially inward in the housing sheath part 3, in a manner perpendicular to the housing sheath flattening. In other words, the protrusion 34 projects downward from the housing sheath part 3. In the drawings, the protrusion 34 projects from the housing sheath part 3 downward into the Albarran lever chamber 12 on the right-hand side of the Albarran lever chamber 12, seen from the distal side. In an alternative, two flat protrusions 34 may protrude downward from the housing sheath part 3 into the Albarran lever chamber 12 on the right-hand and left-hand side of the Albarran lever chamber 12, seen from the distal side. On the end portion opposite to the housing sheath flattening, each of these two protrusions 34 has a passage bore 341 in each of which a shaft end of the Albarran lever shaft 21 is rotatably supported. Then, the Albarran lever is supported in the housing sheath part 3 in a more stable manner.

In embodiment 1, the cover member 5 is screwed to the outer circumference of the endoscope head body 11 by means of two screws, so as to cover the accommodation chamber 11B1. Here, it is also possible to use one screw or more than two screws. Moreover, the cover member 5 may be glued to the outer circumference of the endoscope head body 11, so as to cover the accommodation chamber 11B1. As a further alternative, the cover member 5 may be releasably attached to the outer circumference of the endoscope head body 11 by locking-engagement, so as to cover the accommodation chamber 11B1.

In the second embodiment, the ribs 35 and the grooves 15 may be omitted. The housing sheath part 3 can then be kept closed by the hinge member 310 only and tightly abuts against the endoscope head body 11. The housing sheath part 3 is aligned towards the endoscope head body 11 via the connection between the Albarran lever 20 and the pin 16. In this way, the relative position between the housing sheath part 3 and the endoscope head body 11 is sufficiently specified.

In the first embodiment, the ends of the sheath 31 which are opposed to the flattening 19 and form the edge regions of the attachment opening 32 are formed to be thin on the housing sheath part 3, as it is shown in FIG. 4, for example. In an alternative not shown in the drawings, the ends of the sheath 31 which are opposed to the flattening 19 have a thicker wall thickness and are provided with round U-depressions extending in parallel to the axial direction of the housing sheath part 3. The U-depressions are open towards the attachment opening 32. Round rod elements of an appropriate size can be inserted into the U-depressions. The round rod elements constitute the respective side edges of a plate member (not shown) inserted into the above-mentioned U-depressions from the distal or the proximal side. The round rod elements are formed in one piece with the plate member. The U-depressions have a smaller opening dimension on the open side so as to safely hold the round rods. Thus, the round rod elements can be snap-fitted into the U-depressions and are rotatably supported in the U-depressions. The plate member bridges over and closes the attachment opening 32.

In a similar alternative, one of the two round rod elements of the plate member is fixedly seated in its U-depression of the housing sheath part, is rotatably supported thereon and cannot be pulled out. The other one of the two round rod elements is snap-fitted in its U-depression. Then, the plate member functions in much the same way as the hinge member 310 of the second embodiment. This means, one of the two round rod elements of the plate member is used as pivot bearing of the plate member on the housing sheath part 3 and the other one of the two round rod elements of the plate member is used as a closing member of the plate member on the housing sheath part 3.

Fastening means fastening the housing sheath part 3 to the endoscope head body 11 are described in the embodiments. The rib 35, the groove 15 and the hinge member 310, 320 are specifically mentioned as examples. The invention is not restricted thereto. The term "fastening means" shall include any fastening means suitable to fasten the housing sheath part 3 to the endoscope head body 11. The fastening means may be attached to the housing sheath part 3 or to the endoscope head body 11 or to both of them. It is also possible to use one (or more) external fastening means attached neither to the housing sheath part 3 nor to the endoscope head body 11, such as, for example, an external annular member which is slid on or clamped on the outer circumference of the housing sheath part 3 and the endoscope head body 11 in FIG. 2 of embodiment 1. In case an external fastening means is applied, fastening means attached to the housing sheath part 3 or the endoscope head body 11 (the rib 35, the groove 15 and the hinge member 310, 320) may be omitted.

In the embodiments, the ultrasonic head is arranged on the distal end of the endoscope head, and the endoscope head includes an Albarran lever arranged proximally from the ultrasonic head. The invention may also be applied to an endoscope head including an Albarran lever arranged distally from the ultrasonic head. In this alternative, a working channel and a movement transmission channel are guided past the ultrasonic head. This can be easily accomplished by arranging, with reference to FIG. 1, an ultrasonic head chamber similar to the ultrasonic head chamber 4 between the proximal portion of the endoscope 1 and the endoscope head body 11. The endoscope head body 11 is then arranged on the distal end of the endoscope. The ultrasonic head chamber 4 is arranged proximally of the endoscope head body 11, the bottom region of the ultrasonic head chamber 4 including a working channel portion and a movement transmission channel portion, extending below the ultrasonic head 40 in the bottom region of the ultrasonic head chamber 4 towards the endoscope head body 11.

The described alternatives may be combined and may be applied to all embodiments.

The present invention may preferably be applied to a duodenoscope, a gastroscope, a colonoscope or a similar endoscope. However, the principle of the invention may as well be applied to any other type of endoscope.

LIST OF REFERENCE SIGNS 1 endoscope head
3 housing sheath part
4 ultrasonic head chamber
5 cover member
6 pivot lever
11 endoscope head body
11A side portion for camera and illumination means
11B side portion for pulling wire
11B1 accommodation chamber
11B2 bearing bore
12 Albarran lever chamber
13 working channel
14 pulling wire channel
15 groove (fastening means)
16 pin (operating element)
17 camera
18 illumination means
19 flattening
20 Albarran lever
21 Albarran lever shaft 22 Albarran lever tool pushing surface
31 sheath
32 attachment opening
33 tool opening
34 Albarran lever holder (protrusion)
35 rib (fastening means)
40 ultrasonic head
62 pivot lever rotating shaft
63 pulling wire nipple accommodation
310 hinge member (fastening means)
311 nose
315 engagement groove
320 hinge member (fastening means)
321 nose
322 film hinge
341 bore for Albarran lever shaft

What is claimed is:

1. An ultrasonic endoscope comprising:
an endoscope head body that is disposed on a distal side of an insertion portion of the ultrasonic endoscope and is provided with an Albarran lever chamber which is open continuously at an end portion and a side surface of the endoscope head body;
a convex-shaped ultrasonic head that is disposed at the end portion of the endoscope head body and capable of transmitting and receiving ultrasonic signals in a lateral viewing direction corresponding to the side surface of the endoscope head body;
a hollow cylindrical housing sheath fixed about the endoscope head body and having a flat protrusion extending into the Albarran lever chamber, the housing sheath further fixed to the endoscope head body proximal to the ultrasonic head; and
an Albarran lever that is disposed in the Albarran lever chamber and pivotally fixed to the flat protrusion.

2. The ultrasonic endoscope according to claim 1, wherein the housing sheath is open at an attachment opening provided along a longitudinal direction of the hollow cylinder, and the endoscope head body has a groove that detachably engages with a rib provided at an edge of the attachment opening.

3. The ultrasonic endoscope according to claim 1, wherein the endoscope head body has a flat portion that surrounds three sides of the Albarran lever chamber and extends along a longitudinal direction of the insertion portion.

4. The ultrasonic endoscope according to claim 3, wherein the endoscope head body has a wall extending from the flat portion on a proximal side of the Albarran lever chamber, said wall forming the proximal side of the Albarran lever chamber.

5. The ultrasonic endoscope according to claim 1, wherein the Albarran lever detachably engages with a pin in the Albarran lever chamber, the pin having a rotating shaft, the pin is fixed to a pivot lever that forms the rotating shaft and is rotatably supported by the endoscope head body, and
the pivot lever rotates in conjunction with an operation of an actuating lever provided in an operation unit of the endoscope.

6. The ultrasonic endoscope according to claim 1, wherein the Albarran lever is arranged proximally of the ultrasonic head.

* * * * *